United States Patent [19]
Brisson et al.

[11] Patent Number: 5,301,659
[45] Date of Patent: Apr. 12, 1994

[54] EXTRACORPOREAL SHOCKWAVE LITHOTRIPTER

[75] Inventors: A. Glen Brisson, Kildeer; Exequiel Dela Cruz, Arlington Heights; Dianne L. Vickers, Cary, all of Ill.

[73] Assignee: Bantum Tripter Joint Venture, Columbus, Ohio

[21] Appl. No.: 895,113

[22] Filed: Jun. 8, 1992

[51] Int. Cl.$^5$ .............................................. A61B 17/22
[52] U.S. Cl. ..................................... 601/4; 128/660.03
[58] Field of Search ........ 128/660.03, 24 EL, 24 AA, 128/653.1; 378/197, 198

[56] References Cited

U.S. PATENT DOCUMENTS

| | | | |
|---|---|---|---|
| 4,432,359 | 2/1984 | James | 128/869 |
| 5,036,836 | 8/1991 | Terai et al. | 128/24 EL |
| 5,067,145 | 11/1991 | Siczek et al. | 378/198 |

*Primary Examiner*—Ruth S. Smith
*Attorney, Agent, or Firm*—Robert M. Wolters

[57] ABSTRACT

An extracorporeal lithotripter has a base mounted on wheels for movement about a floor or the like. There is an upright extensible support on the base caring a horizontal extensible support. The horizontal support has a swivel at its outer end with a pair of diverging arms pivotably carrying a truncated ellipsoidal reflector having an otherwise open end closed by a flexible membrane. A spark gap is disposed at the first focal point of the reflector. The second focal point is beyond the membrane and is to be placed on a kidney stone or the like to be disintegrated. Parts are manually movable, and an electric screw jack controls extension of the upright support. The movable parts are all locked by electric brakes except when a pushbutton switch is pushed and held to unlock the brakes for movement of the movable parts. The lithotripter is remarkably simple, rugged and inexpensive.

10 Claims, 3 Drawing Sheets

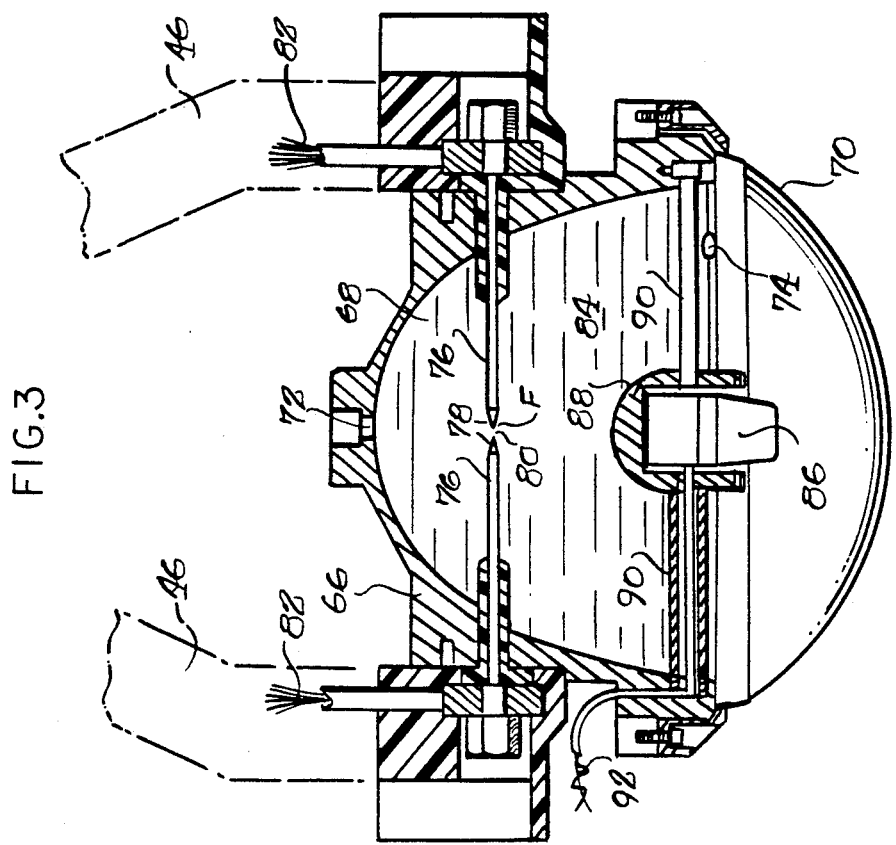
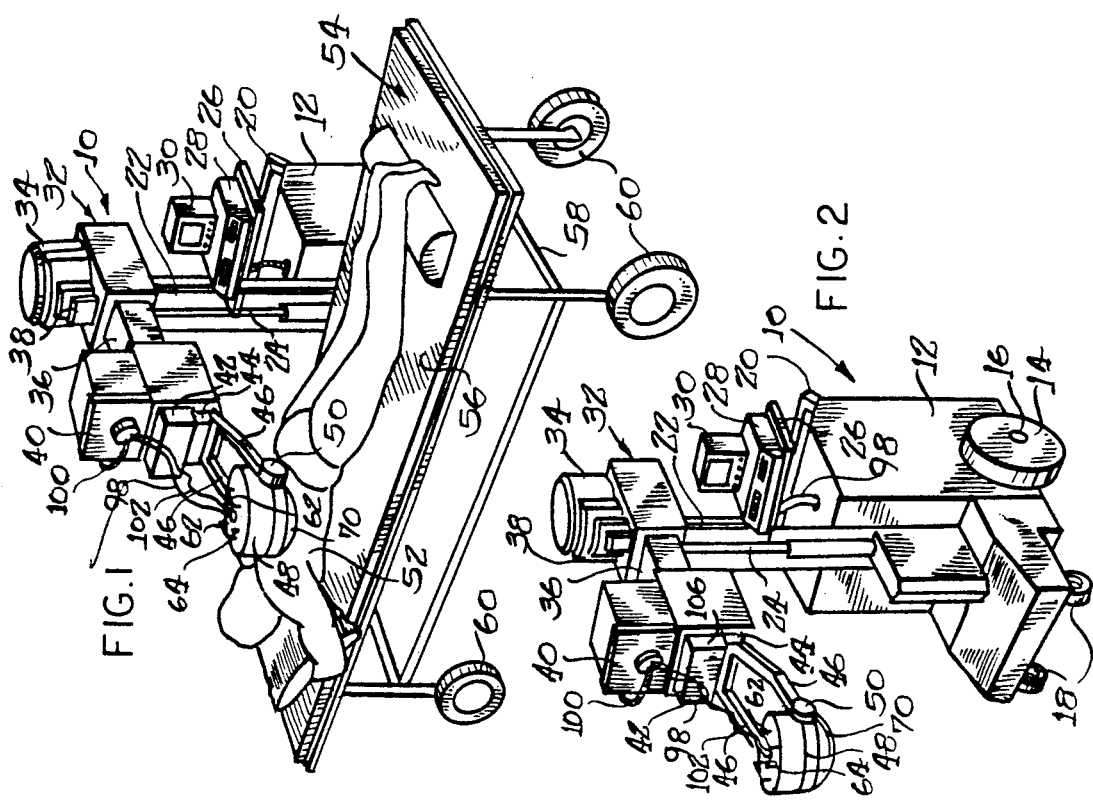

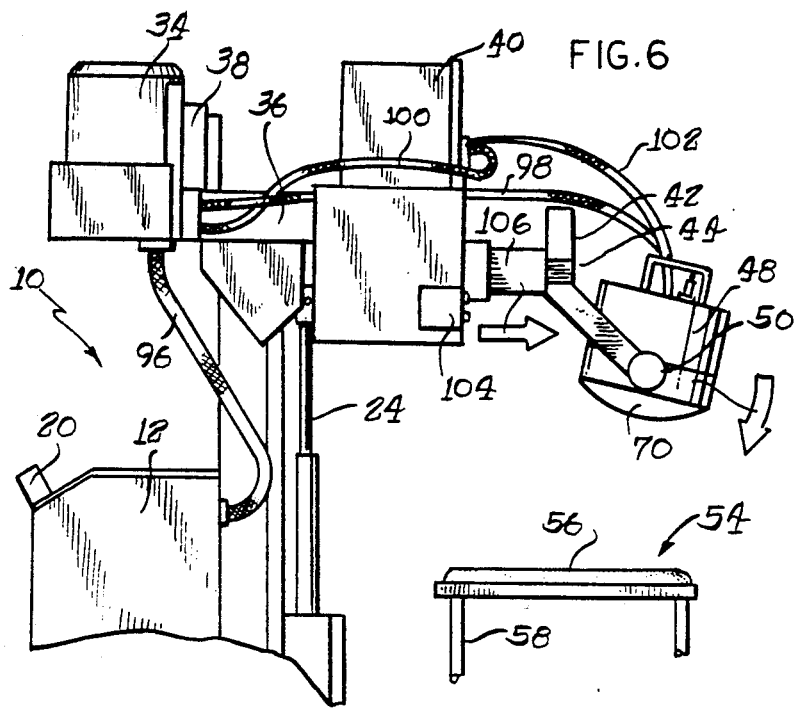
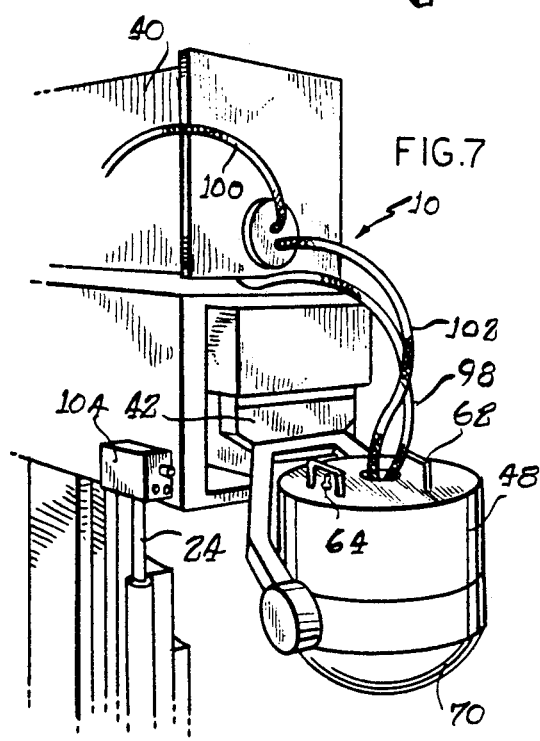
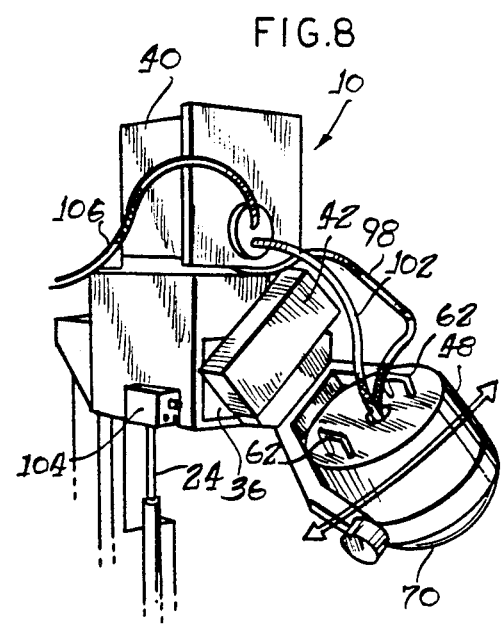

EXTRACORPOREAL SHOCKWAVE LITHOTRIPTER

RELATED APPLICATIONS

There are four copending applications disclosing greater detail of parts of the lithotripter disclosed in the present application. These are all in the names of A. Glen Brisson, Exequiel Dela Cruz and Dianne L. Vickers. These copending applications are Ser. No. 07/856352, now abandoned, WATER SYSTEM FOR LITHOTRIPTER; Ser. No. 07/856374 now U.S. Pat. No. 5,203,334 for TRANSDUCER MOUNTING IN LITHOTRIPTER; Ser. No. 07/856373 now U.S. Pat. No. 5,240,002 ULTRASOUND TRANSDUCER SHIELDING; and Ser. No. 07/856375 for LITHOTRIPTER ELECTRODES. These four applications bear a common filing date of Mar. 23, 1992.

BACKGROUND OF THE INVENTION

Surgery for kidney stones is traumatic to the patient in general, and specifically to the kidney operated upon. Typically, a kidney will withstand no more than three such surgical operations without shutting down. Extracorporeal shockwave lithotripters have in most cases rendered such surgery unnecessary. As is known, an ellipsoid of revolution has two focal points. A reflector comprises a truncated ellipsoid which has a pair of electrodes spaced apart to define a sparkgap precisely at the first focus point of the ellipsoid. A rubber or the like diaphragm covers the truncated, open end of the ellipsoidal reflector. The reflector is filled with water having a sufficient saline content to make it conductive. The reflector is positioned with the diaphragm at the end thereof against the patient's body such that the second focus point of the ellipsoidal reflector lies precisely on the kidney stone to be disintegrated. High voltage electrical pulses generate a series of sparks in the gap between the electrodes. Each such spark flashes a certain amount of water into steam, and may actually dissociate a certain amount of the water. A shockwave is generated which is reflected by the ellipsoidal reflector to focus precisely on the kidney stone. The shockwave energy passes through the water in the reflector, through the diaphragm, and through human tissue which is mostly water. Within an hour the kidney stone is usually reduced to fine particles that pass from the body along with the urine.

Such extracorporeal lithotripters are quite expensive, often measured in millions of dollars. This limits availability of such lithotripters to large hospitals and the like having sufficient capital to finance purchase of such lithotripters. In addition to the cost, most such lithotripters are interconnected with computers to effect positioning of the reflector and to control operation of the lithotripter. Many physicians are unfamiliar with computers and are somewhat "put off" in having/to use computer controlled devices.

Some of the prior art extracorporeal lithotripters have required that the patient and the reflector be immersed in a rather large water bath. Those that have not required immersion have generally required that the patient lie on his back on a table having a hole or recess therein to permit the reflector to approach his back from below. Electrical or electrical/mechanical devices of considerable complexity and cost have generally been required for proper positioning of the lithotripter reflector adjacent the patient's body.

OBJECTS AND SUMMARY OF THE PRESENT INVENTION

It is the primary object of the present invention to provide an extracorporeal lithotripter relatively simple in nature, inexpensive, and easy to operate.

A further object of the present invention is to provide an extracorporeal lithotripter in which the ellipsoidal head or reflector is manually controllable in a horizontal plane, and manually controllable with electrical power assist for up and down movement.

In accordance with the present invention a simple extracorporeal lithotripter is provided somewhat in the nature of a portable x-ray machine. The lithotripter is self-contained. It has a horizontal arm supporting the reflector, which arm is manually telescoped for moving of the reflector in a horizontal direction transverse of the patient. Movement in a horizontal plane perpendicular to the supporting structure is effected by wheeling the patient table in either direction along its major axis. The supporting structure for the reflector can be moved in part manually, and is assisted by an electric screw jack to run the supporting structure vertically up or down. Electric brakes are provided on the moving parts which are normally in braking position to prevent any of the parts from moving accidentally. A pushbutton switch is provided for unlocking the brakes when it is desired to effect movement of the reflector. Release of the push-button causes the brakes to apply automatically.

The water supply is entirely self-contained so that the lithotripter does not have to be permanently interconnected with a water supply. The reflector overlies the patient's body with the patient lying on his abdomen. The water in the reflector is maintained under low pressure to prevent undue extension of the membrane or diaphragm which is intended to contact the patient's back in the vicinity of the kidney having the stone. The reflector generally is above the patient, but the mounting structure can be pivoted about a horizontal axis for placement of the reflector below the patient if this should be desirable. In addition, this rotation about a horizontal axis is coupled with pivoting about a right angle horizontal axis to allow angular disposition of the reflector in any necessary position.

An ultrasound transducer is disposed within the reflector on the principle axis (axis of rotation) of the reflector, and is used in combination with a monitor or display apparatus for showing the position of the stone relative to the reflector. Computer operation is totally dispensed with and manual positioning of the lithotripter and the patient table allows the relative position of the kidney stone or other target with reference to the ultrasound transducer to be viewed on the display screen for accurate positioning of the reflector relative to the stone.

THE DRAWINGS

The present invention will best be understood from the following specification when taken in connection with the accompanying drawings wherein:

FIG. 1 is a perspective view of an extracorporeal lithotripter constructed in accordance with the present invention;

FIG. 2 is a view generally similar to FIG. 1 with the patient and table removed for viewing the lower portion of the lithotripter;

FIG. 3 is an axial sectional view through the reflector on an enlarged scale;

FIG. 6 is a fragmentary view similar to FIGS. 4 and 5 showing the tilting or swivelling of the reflector;

FIG. 7 is a further enlarged perspective view of the lithotripter reflector and support therefore showing the reflector aimed straight down; and FIG. 8 is a view similar to FIG. 7 showing the reflector pivoted about the horizontal axis in the lithotripter's supporting arm.

DETAILED DISCLOSURE OF THE ILLUSTRATED EMBODIMENT

Figure 4:
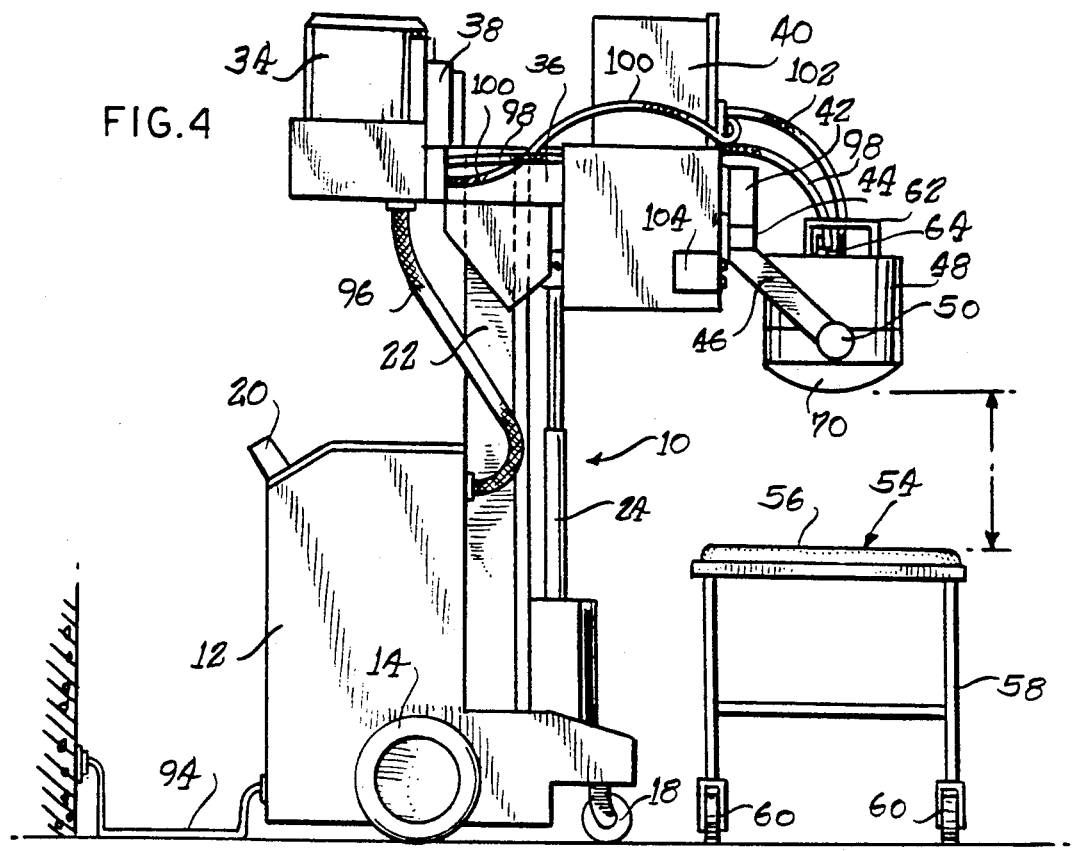
FIG. 4 is a side view of the lithotripter as in FIG. 1, taken generally from the left side of the figure.

Turning now in greater particularity to the figures of the drawings, and first to FIGS. 1 and 2, there will be seen a lithotripter 10 constructed in accordance with the principles of the present invention. The lithotripter 10 includes a base unit 12 having a pair of large wheels 14 rotatable about aligned axes 16. Smaller wheels 18 which are pivotable about vertical axes are mounted relatively toward the left end of the lithotripter as viewed in FIGS. 1 and 2. A fairly large transverse handle 20 is provided at the top rear portion of the base unit for aid in moving the lithotripter. The base unit houses a water storage tank and portions of the electronics. Further details on the water system including the tank may be seen in our copending application Ser. No. 07/856352, previously referenced.

The lithotripter further includes an upright support or stand 22 which is telescopicly extensible, and which includes a telescoping screw jack 24 operated by an electric motor to aid in raising and lowering the vertical stand and parts supported thereby. A table 26 extends from the support 22 and carries thereon a base 28 and monitor 30 of an ultrasound unit. The ultrasound unit is used in aiming the lithotripter at a patient.

Top supporting structure 32 extends from the vertical support 22, and is capable of being moved up and down by the screw jack 24. A secondary water tank 34 is mounted on the vertical support structure somewhat to the rear of the vertical support 22 and provides a counterweight for forwardly extending arm or support member 36. A housing 38 substantially above the vertical support 22 carries portions of the electrical circuits of the lithotripter. Further forwardly on the forwardly projecting and horizontally disposed arm 36 there is a housing 40 for the spark discharge circuit of the lithotripter. I.e., the high voltage capacitor is disposed within this housing, and is charged and subsequently discharged to generate the necessary spark. The arm 36 extends forwardly of the housing 40, and has a swivelling head 42 carrying a yoke 44. The head 42 is pivotable about a horizontal axis which extends lengthwise of the arm 36. The yoke further includes a pair of diverging arms 46 to which a reflector housing 48 is pivoted about an initially horizontal axis, utilizing connectors 50 at the end of each arm 46.

For use of the lithotripter a patient 52 lies on his abdomen on an operating table 54. The operating table is a conventional hospital transporting table including a padded horizontal support surface 56 and an undercarriage 58 having wheels 60 mounted thereon. The wheels may be mounted for motion of the table in its long direction, or two of the wheels may be pivoted in addition to allow steering. As will be understood, the wheels are lockable to secure the table in a fixed position. The table may be of standard construction, and does not require a cutout over which the patient must lie for access from below. The reflector housing is disposed above the patient in alignment with the kidney stone or other concretion to be destroyed.

The housing 48 is provided with a pair of spaced apart hand grips 62 on the top thereof. A pushbutton brake releasing switch 64 is disposed on the top of the housing adjacent to one of the hand grips. All of the movements of the lithotripter, as set forth more fully hereinafter, are normally secured in position by commercially available brakes. The brakes are normally in set position. Depression of the pushbutton switch 64 electrically retracts the brakes for desired movement of the movable portions of the lithotripter. Upon release of the pushbutton switch 64 the parts are instantly locked in position.

Construction of the lithotripter reflector and shockwave generator is shown generally in FIG. 3. The housing 48 is omitted, but the arms 46 of the yoke 44 are shown in phantom for parts relation. The reflector includes a metallic structure 66/the inside of which is shaped as a reflector surface 68 forming a part of an ellipsoid of revolution having a first focus point F. The ellipsoid is truncated, and the lower, open end thereof is closed by a rubber or the like diaphragm or membrane 70 which bulges convex downwardly. This diaphragm engages the patient's back as may be seen in FIG. 1. The reflector is provided at its apex with a water circulating opening 72, and a second water circulating opening 74 is provided substantially at the rim of the reflector. These are connected through suitable flexible hoses to the water tank 34, and to the water supply tank within base 12.

Electrodes 76 are mounted by suitable insulating structure in the metallic structure 66 and extend coaxially toward one another, being terminated with tapered tips 78 forming a spark gap 80 which is coincident with the first focal point F. Electrical conductors 82 which are suitably insulated extend from the electrodes 76 to the housing 40 to provide a short path from the discharging capacitor to the electrodes to provide a very short electrical path minimizing electrical loss, and preserving the high frequency components of the electrohydraulic shockwave. Those skilled in the art of lithotripters will realize that the reflector and the diaphragm or membrane are filled with water 84 during operation, the water having sufficient saline content to be appropriately conductive. A spark across the gap 80 flashes a certain amount of water into steam, and may actually dissociate some of the water. This creates a shockwave which is reflected by the walls of the reflector 68 to pass through the diaphragm 70 and through human tissues to the second focus point of the reflector which is placed in coincidence with the kidney stone or the like to be destroyed.

Substantially at the lower rim of the reflector there is provided an ultrasound transducer 86 which is disposed within a protective metal housing 88 and supported by arms 90 on the axis of rotation of the reflector 68. The ultrasound transducer 86 is connected by wires 92 to the ultrasound unit 28 and monitor 30. Further details on the reflector and the electrodes and ultrasound transducer mounting will be found in our previously referenced applications Ser. No. 07/856374 for TRANSDUCER MOUNTING AND LITHOTRIPTER; Ser. No. 07/856373 for ULTRASOUND TRANSDUCER SHIELDING; and Ser. No. 07/856375 for LITHOTRIPTER ELECTRODES.

Certain operational parts and features are illustrated in FIGS. 4–8. For example, in FIG. 4 an electrical line cord 94 providing power to the lithotripter is shown plugged into an appropriate wall outlet. A flexible hose 96 provides for water movement from a storage tank in the base 12 to the top mounted tank 34. An additional dual hose unit 98 leads from the tank 34 to the reflector.

The ultrasound unit 28 and monitor 30 are not shown in FIG. 4 and 8, as these parts may be more readily disposed on a separate table or the like. Wires or cables are shown generally at 100 leading from the housing 38 to the capacitor housing 40, and an additional wire or cable 102 containing the discharge wires 82 and the ultrasound device wires 92 extend through a cable 102 from the housing 90 into the reflector housing 48.

Figure 5:
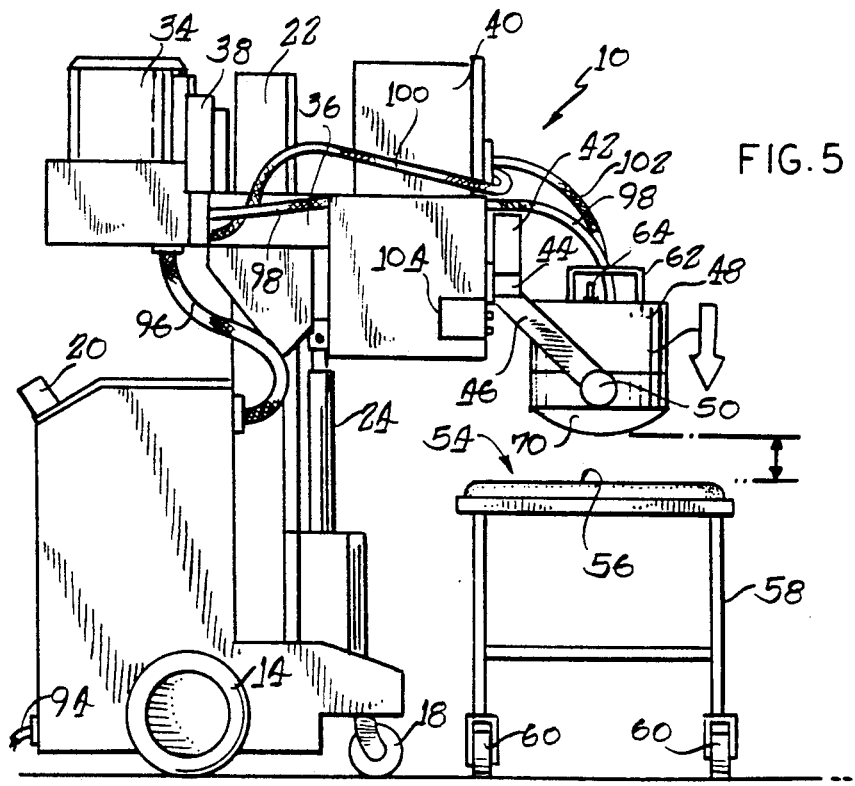
FIG. 5 is a view similar to FIG. 4 showing the reflector in a lowered position as compared with FIG. 4.

A switch unit 104 is at a convenient location, such as on the side of the upper support structure for control of the motor running the electric screwjack 24 to raise and lower the upper structure. FIGS. 4 and 5 considered together illustrate the manner in which the upper structure, particularly including the reflector housing 48 can be raised or lowered relative to the top padded surface 56 of the table 54. FIG. 6, contrasted with FIG. 4, 5 and 7, shows how the arm 36 at the forward portion thereof offset is extensible, identified at 106. As will be understood, this extension or telescoping back together is effected manually with the release switch button 64 depressed. The same contrast also shows the manner in which the reflector housing 48 is pivotable about a horizontal axis between the supports 50 at the ends of the yoke arms 46. FIG. 8, contrasted with FIG. 4–7, shows the pivoting of the yoke and of the reflector and housing about a horizontal axis coincident with the extensible part 106 of the arm 36. The swivelling and tilting illustrated in FIGS. 8 and 6 will be understood as being manually controlled, and locked by electric brakes upon release of the pushbutton switch 64.

The ultrasound transducer 86 and the ultrasound unit 28 and monitor 30 are utilized for aligning the reflector with the kidney stone or other concretion to be destroyed. All of this is done manually, as previously noted, thereby reducing complexity and cost. The diaphragm is pressed against the patient's back and suitable swivelling of the reflector shows alignment thereof with the stone. The caliper feature of the ultrasound system is well known in the art, and indicates the distance of the stone from the ultrasound transducer 68 for insuring that the second focus point of the reflector is precisely on the stone to be destroyed.

As will be apparent, the lithotripter 10 is compact and readily moved about manually upon grasping of the handle 20. The table 54 is movable longitudinally of itself for adjustment relative to the lithotripter. The use of manual adjustments throughout with the addition of the electric screwjack 24 materially simplifies the construction of the lithotripter, and thereby holds the cost within reason. Further, there is no computer, thereby further minimizing costs and rendering operation straightforward and clear to those who are not familiar with the use of computers.

Various changes in structure will no doubt occur to those skilled in the art, and will be understood as forming a part of the present invention insofar as they fall within the spirit and scope of the appended claims.

The invention is claimed as follows:

1. A lithotripter comprising a base, rotary means on said base for movement of said lithotripter about a supporting surface, an extensible upright support on said base and extending substantially vertically upward therefrom, a substantially horizontal support carried by said extensible upright support, means for varying the height of said substantially horizontal support with the degree of extension of said extensible support, said substantially horizontal support having an extensible portion means for linearly moving said extensible portions toward and away from said upright support, a reflector having an open end, means for generating a shock wave in said reflector, a flexible membrane covering said reflector open end, and means for supporting said reflector including a swivel mounting said reflector from said extensible portion of said substantially horizontal support, and said swivel including a forked member pivotally connected to said extensible portion for pivoting about a horizontal axis, said forked member having a pair of arms lying on opposite sides of and connected to said reflector for pivoting of said reflector about an axis perpendicular to said horizontal axis, said swivel being adapted to permit movement of said reflector to position said flexible membrane against a patient with said reflector aimed at a bodily concretion to be disintegrated.

2. A lithotripter as set forth in claim 1 wherein said reflector, said swivel, and said extensible portion of said substantially horizontal support include means adapted to be engaged manually for manual movement of said reflector, said swivel and said extensible portion.

3. A lithotripter as set forth in claim 2 and further including brakes normally locking said reflector, said swivel, said extensible portion of said substantially horizontal support, and means for manually releasing said brakes.

4. A lithotripter as set forth in claim 3 wherein said brakes comprise electric brakes.

5. A lithotripter as set forth in claim 1 and further including brakes normally locking said reflector, said swivel, said extensible portion of said substantially horizontal support and means for manually releasing said brakes.

6. A lithotripter as set forth in claim 5 wherein said brakes comprise electric brakes.

7. A lithotripter as set forth in claim 1 and further including at least one handgrip on said reflector for moving said reflector.

8. A lithotripter as set forth in claim 7 and further including normally engaged electric brakes acting on said reflector, said swivel and said extensible portion of said substantially horizontal support, and a manually engagable switch means on said reflector adjacent said at least one handgrip on said reflector for unlocking said electric brakes.

9. A lithotripter as set forth in claim 1 and further including a jack operating between said base and said substantially horizontal support to control extension of said extensible upright support.

10. A lithotripter as set forth in claim 9 wherein said jack includes an electrical screw jack vertically disposed between said base and said horizontal support and spaced from said upright support toward said extensible portion.

* * * * *